US005656424A

United States Patent [19]

Jurgensen et al.

[11] Patent Number: 5,656,424

[45] Date of Patent: Aug. 12, 1997

[54] **IDENTIFICATION OF *MYCOBACTERIUM TUBERCULOSIS* COMPLEX SPECIES**

[75] Inventors: Stewart Jurgensen; Michael C. Little, both of Raleigh; Paul T. Hamilton, Cary, all of N.C.; Paul Riska, Bronx, N.Y.; John Chan, Yonkers, N.Y.; Barry R. Bloom, Hasting on Hudson, N.Y.

[73] Assignee: Albert Einstein College of Medicine, a Division of Yeshiva University, Bronx, N.Y.

[21] Appl. No.: 388,916

[22] Filed: Feb. 15, 1995

[51] Int. Cl.$^6$ ..... C12Q 1/70; C12Q 1/66; C12Q 1/18; C12N 1/20

[52] U.S. Cl. ..... 435/5; 435/8; 435/32; 435/34; 435/172.3; 435/253.1

[58] Field of Search ..... 435/5, 8, 253.1, 435/172.3, 32, 34

[56] References Cited

FOREIGN PATENT DOCUMENTS 9316172 8/1993 WIPO .

OTHER PUBLICATIONS

Laszlo, A. and Siddigi, S.H. 1984. Evaluation of a Rapid Radiometric Differentiation Test for the *Mycobacterium tuberculosis* Complex by Selective Inhibition with p–Nitro–α–Acetyamine–β–Hydroxypropiophenone, Journal of Clinical Microbiology, 1965), 694–698.

*Primary Examiner*—Douglas W. Robinson
*Assistant Examiner*—Thanda Wai

[57] ABSTRACT

Methods for using reporter mycobacteriophage (RM) and p-nitro-α-acetylamino-β-hydroxy-propiophenone (NAP) to identify TB complex mycobacteria and distinguish these species from MOTT. RM-infected MOTT show little or no reduction in signal when treated with NAP. In contrast, TB complex mycobacteria infected with RM are distinguishable from RM-infected MOTT by a reduction in signal with NAP treatment.

30 Claims, 2 Drawing Sheets

IDENTIFICATION OF *MYCOBACTERIUM TUBERCULOSIS* COMPLEX SPECIES

FIELD OF THE INVENTION

The invention relates to detection and identification of microorganisms, and in particular to detection and identification of microorganisms of the *Mycobacterium tuberculosis* (M.tb.) complex. This work was supported in part by grant No. CCR209585-01 from the Centers for Disease Control to John Chan.

BACKGROUND OF THE INVENTION

The Mycobacteria are a genus of bacteria which are acid-fast, non-motile, gram-positive rods. The genus comprises several species which include, but are not limited to, *Mycobacterium africanum, M. avium, M. bovis, M. bovis-BCG, M. chelonae, M. fortuitum, M. gordonae, M. intracellulare, M. kansasii, M. microti, M. scrofulaceum, M. paratuberculosis and M. tuberculosis*. Certain of these organisms are the causative agents of disease. For the first time since 1953, cases of mycobacterial infections are increasing in the United States. Of particular concern is tuberculosis, the etiological agent of which is *M. tuberculosis. M. tuberculosis* and other mycobacteria which are closely related to M.tb. (*M. bovis, M. africanum, M. tuberculosis BCG and M. microti*) are referred to as the TB complex mycobacteria. Many of these new cases of mycobacterial infection are related to the AIDS epidemic, which provides an immune compromised population which is particularly susceptible to infection by Mycobacteria. Mycobacterial infections other than tuberculosis are also increasing as a result of recent increases in the number of immune compromised patients. For example, *Mycobacterium avium, Mycobacterium kansasii* and other non-tuberculosis mycobacteria are found as opportunistic pathogens in patients infected with HIV as well as in in other immune compromised patients.

In recent years there has also been an increase in the number of clinical isolates of tuberculosis which are resistant to at least one of the antibiotics normally used to treat the disease (e.g., isoniazid, rifampin or streptomycin). Multidrug-resistant tuberculosis strains have emerged in several countries, resulting in a corresponding increase in the number of fatalities in both immunocompetent and immunocompromised individuals. Because M.tb. grows very slowly (doubling time 20–24 hrs.), conventional methods for identifying this organism and determining drug susceptibility require 2–18 weeks. During that time, patients are often treated empirically with antibiotics which may be ineffective, as lack of any treatment allows the patient to remain infectious and puts the patient and patient contacts at risk. Such empirical treatment can also exacerbate the development of drug resistance.

Conventional diagnosis of mycobacterial infections is dependent on acid-fast staining and cultivation of the organism, followed by biochemical and morphological assays to confirm the presence of mycobacteria and identify the species. These procedures are time-consuming, and a typical diagnosis using conventional culture methods can take as long as six weeks. Automated culturing systems such as the BACTEC™ system (Becton Dickinson Diagnostic Instrument Systems, Sparks, Md.) can decrease the time for detection of mycobacteria to one to two weeks. Once detected, culturing these slow-growing microorganisms in the presence of antibiotics to determine their drug susceptibility requires several additional weeks. There is still a need to reduce the time required for diagnosing mycobacterial infections and determining antibiotic susceptibility even further in order to allow prompt, informed treatment of M.tb. infections.

The BACTEC TB System provides one means for determining whether or not a positive mycobacterial culture is the result of TB complex mycobacteria or mycobacteria other than tuberculosis (MOTT). This is important information for the initial diagnosis of tuberculosis, and shortens the time required for determining the species present in a positive mycobacterial culture. The BACTEC identification scheme relies on a combination of three tests, namely, morphology on smear, growth characteristics and the NAP (p-nitro-α-acetylamino-β-hydroxy-propiophenone) TB differentiation test. NAP is an intermediate compound in the synthesis of chloramphenicol which markedly inhibits the growth mycobacteria belonging to the TB complex. MOTT show little or no growth inhibition, and any slight inhibition of growth is usually temporary. The mechanism of action of NAP on TB complex mycobacteria is not known, nor is the reason for its TB complex-specificity. When cultured in the presence of NAP, TB complex organisms show sharply reduced evolution of $CO_2$, whereas MOTT continue to grow with increasing $CO_2$ production. The BACTEC TB System measures $CO_2$ evolution, as a "growth index" (GI) by monitoring production of $14_C$-labeled $CO_2$ in cultures containing $14_C$-labeled palmitate. Once a positive culture is obtained, speciation by determining growth ($CO_2$ production) in the presence of NAP generally requires an additional 4–6 days.

Luciferase is useful as a biological reporter or signal generating molecule because it catalyzes the reaction of luciferin with adenosine triphosphate (ATP), resulting in the production of light. Sensitive light-detection systems are available to detect and measure light (luminescence) generated by this reaction. Luciferase has been used for many years in the standard assay for measuring ATP. The cDNA coding for firefly luciferase (FFluc) has been cloned, which has allowed its use as a direct reporter molecule in a variety of transformed and transfected cells. In mycobacteria, FFluc has been inserted into the genomes of mycobacteriophage and into plasmids as a reporter gene for use in antibiotic susceptibility testing as an in vivo measure of cell viability after exposure to antibiotics. W. R. Jacobs, et al. (1993) *Science* 260:819 and WO 93/16172. Inhibition of culture growth results in reduced or absent light production from the cloned luciferase gene. This effect has been attributed to reduced amounts of ATP (required for the luciferase reaction) in antibiotic-sensitive cells, which exhibit reduced metabolic activity in the presence of an anti-TB antibiotic.

β-galactosidase is an enzyme which cleaves lactose into glucose and galactose. Other substrates for this enzyme are also known. X-gal (5-bromo-4-chloro-3-indolyl-β-D-galactoside) and chlorophenol red-β-D-galactopyranoside are colorimetric substrates for β-galactosidase. Enzymatic cleavage of X-gal produces a reaction product which is blue in color. Enzymatic cleavage of chlorophenol red-β-D-galactopyranoside produces a reaction product which is yellow to red in color. Methyl umbelliferyl-β-D-galactopyranoside is a fluorometric substrate for β-galactosidase which produces a fluorescent signal when enzymatically cleaved. This ability to produce a signal makes β-galactosidase useful as a reporter molecule in conjunction with colorimetric or fluorometric the enzymatic substrates, and these signal generating systems have been used in a variety of biological assays. Like FFluc, the bacterial gene which encodes β-galactosidase (LacZ) has been cloned and used as a reporter gene in recombinant organisms in both inducible and constitutive expression systems.

As used herein, the term "reporter gene" refers to a gene which can be expressed to produce a gene product which directly or through further reaction generates a detectable signal. This signal can be used to detect or identify cells carrying the gene, either on a plasmid or inserted into the genome of the cell. Examples of reporter genes are the gene encoding firefly luciferase (resulting in a luminescent signal upon reaction with luciferin) and the gene encoding β-galactosidase (resulting in a colored or fluorescent signal upon reaction with appropriate enzyme substrates). A mycobacteriophage carrying a reporter gene is referred to herein as a "reporter mycobacteriophage" or "RM." Mycobacteriophage carrying a luciferase reporter gene are referred to as "luciferase reporter mycobacteriphage" or "LRM." Mycobacteriphage carrying a β-galactosidase reporter gene are referred to as "β-galactosidase reporter mycobateriphage" or "β-GRM."

The host range of mycobacteriophage varies greatly, with some capable of infecting only a single species. Certain mycobacteriophage (e.g., TM4 or phAE40) have been characterized as preferentially infecting species of the TB complex, whereas others (e.g., L5) have a very broad range of mycobacterial hosts. A reporter mycobacteriophage constructed in TM4 or phAE40 would therefore be expected to be useful for specific identification of TB complex organisms, as primarily TB complex species should be infected and produce a signal. However, in practice, these mycobacteriophage are not perfectly species-specific, infecting and producing high levels of signal in certain MOTT species as well. This results in false-positives which are unacceptable for clinical detection and identification of TB complex mycobacteria. The present invention not only meets the need for a more rapid method for detection, identification and antibiotic susceptibility testing of TB complex organisms, it solves the problem of identifying false-positives and provides more accurate identification of TB complex organisms using a reporter mycobacteriophage.

SUMMARY OF THE INVENTION

The present invention uses luciferase reporter mycobacteriophage or β-galactosidase reporter mycobacteriphage and NAP to identify TB complex organisms and distinguish them from MOTT. As the mechanism of TB complex growth inhibition by NAP is not known, it was not known prior to the present invention whether NAP inhibition of bacterial growth would affect the production of light by LRM or affect the production of a reaction product by β-GRM. That is, it was not known prior to the present invention whether or not exposure to NAP would result in reduced production of light by a luciferase reporter mycobacteriophage and, if so, whether or not reduced light production could be used to distinguish TB complex organisms from MOTT. It was also unknown whether or not exposure to NAP would result in a reduction in β-galactosidase reaction products produced by β-galactosidase reporter mycobacteriophage and, if so, whether or not this response could be used to distinguish these species of mycobacteria. It has now been discovered that use of the luciferase reporter gene or the β-galactosidase reporter gene in place of $CO_2$ measurements in the conventional NAP identification system allows TB Complex vs. MOTT species identification in 48 hours or less. In many cases identification can be made in as little as 1–3 hours. The successful assays performed with these two reporter genes suggest that many of the reporter genes known in the art may be substituted in the RM/NAP assays of the invention with similar results.

Further, in conjunction with antibiotic susceptibility testing, the RM/NAP identification system the invention allows more information to be obtained from a determination of antibiotic susceptibility. Antibiotic resistant MOTT and antibiotic resistant TB complex organisms infected with RM both produce a positive signal when cultured in the presence of the antibiotic. However, a positive signal (e.g., luminescence from luciferin or a colored reaction product from a colorimetric substrate for β-galactosidase) which is due to an antibiotic-resistant TB complex organism is substantially reduced upon exposure to NAP, whereas antibiotic-resistant MOTT continue to produce a signal when treated with NAP.

DETAILED DESCRIPTION OF THE INVENTION

Figure 1:
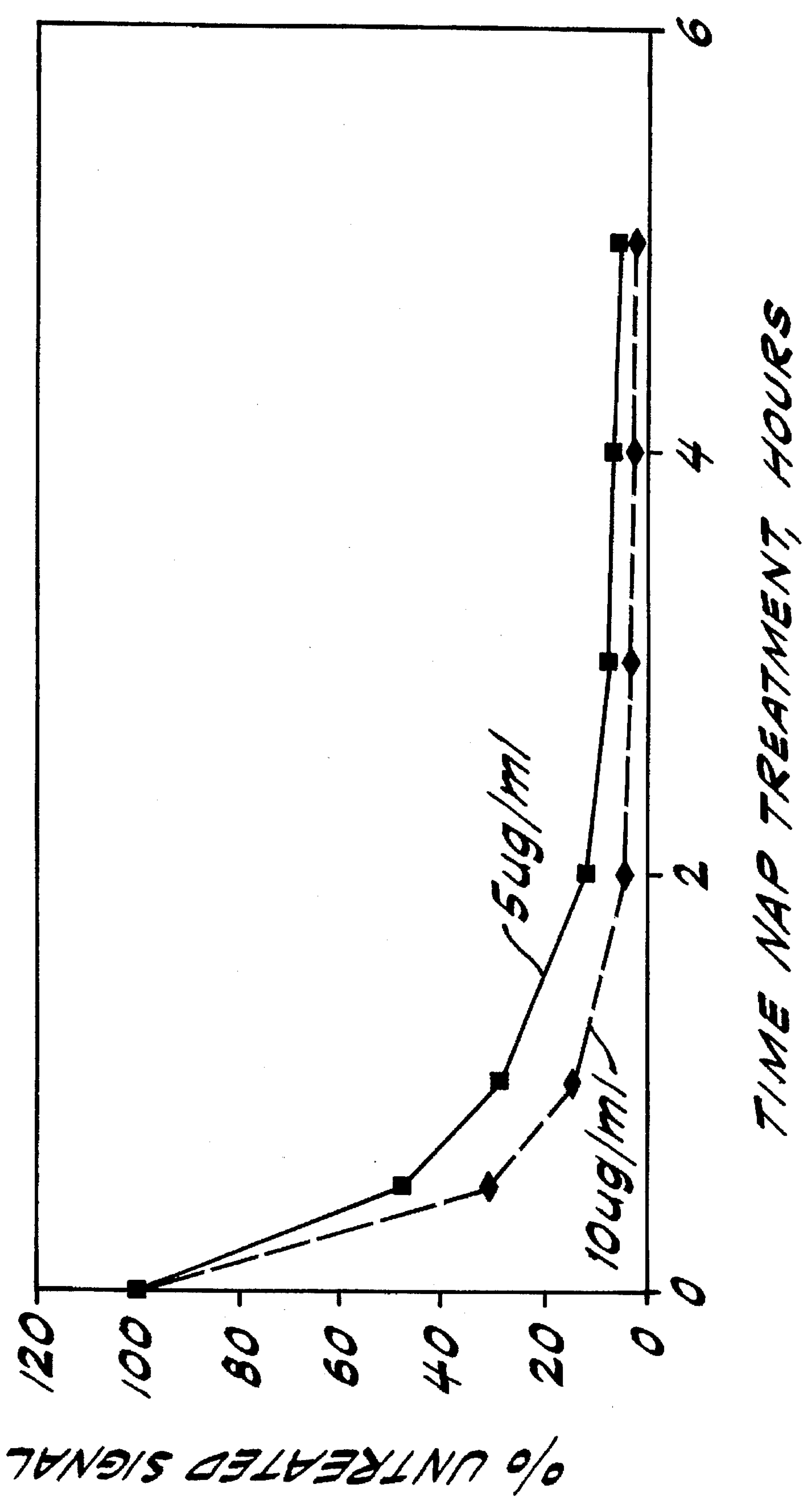
FIG. 1 is a graph showing the time course of the reduction in luminescence of phage phAE42-12-infected *M. bovis* BCG in response to NAP treatment.

The invention provides methods for clinical identification or antimicrobial susceptibility testing of *M. tuberculosis* and other TB complex organisms using a reporter mycobacteriophage assay and the differential effect of NAP on the growth of mycobacteria species. The inventive methods not only allow rapid identification of TB complex organisms, they distinguish between a false-positive signal arising from MOTT infected by the reporter mycobacteriophage and a true positive signal arising from phage-infected TB complex organisms. The methods may also be adapted to determine antibiotic susceptibility, distinguishing between a positive signal arising from an antibiotic-resistant TB complex organism and a positive signal arising from antibiotic resistant MOTT.

Applicants have for the first time demonstrated that NAP treatment can be used in a reporter phage assay to distinguish between TB complex organisms and MOTT. The mechanism of TB-complex-specific growth inhibition by NAP is not well understood, although it was previously known that growth inhibition was accompanied by reduced $CO_2$ evolution by cultures. Of significance to the present invention, however, is that it was not previously known whether or not NAP treatment would also selectively inhibit luminescence in TB complex organisms in an LRM assay, as several mechanisms of NAP-induced growth inhibition which would not affect the intracellular level of ATP could be hypothesized (e.g., cell surface effects, inhibition of transcription or translation factors, etc.). Whether or not NAP would inhibit processes necessary for the production of colored or fluorescent reaction products in the β-GRM assay was also unknown. It has now been discovered that mycobacteria cultured in a suitable liquid media can be treated with NAP in an amount sufficient to inhibit growth of TB complex mycobacteria, and detected in an LRM assay such as the assay described by W. R. Jacobs, et al. and in WO 93/16172, supra, to distinguish TB complex from MOTT organisms by reduction in luminescence. Alternatively, NAP inhibition of growth of TB complex organisms may be detected as reduced production of colored or fluorescent reaction products in a β-GRM assay.

The following discussion employs LRM as an example. However, it is equally applicable to β-GRM as well as other RM carrying other reporter genes. In the conventional LRM assay, mycobacterial cells are infected with the LRM and begin to synthesize luciferase by expression of the cloned gene carried by the reporter mycobacteriophage. Upon addition of luciferin, infected cells emit a signal (luminescence), whereas uninfected cells do not. Identification of the species of mycobacteria should therefore be possible by selection of a RM with the desired host range. However, the RM's currently available are not perfectly specific for the TB complex organisms. Although they do not infect all MOTT, many MOTT species produce high luminescence signals due to infection with "TB complex-specific" LRM such as those derived from TM4 and phAE40 . For example, luciferase reporter mycobacteriophage phAE42-12 is a mutant of phAE40 isolated for increased luminescence signal and deposited with the American Type Culture Collection (Rockville, Md.) on Feb. 7, 1995 as Accession Number ATCC 97046. phAE40 is a mutant derived from TM4, selected for broadened range of infection of TB complex organisms. Like its parent phage, phAE42-12 efficiently infects *M. flavescens, M. smegmatis, M. intracellulare* and *M. chelonae* and gives high luminescence signals. phAE42-12 generally does not infect *M. fortuitum; M. gordonae, M. kansasii* and *M. xenopi*, but certain strains of these species have been found which are inefficiently infected. Similarly, although many strains of *M. avium* do not support infection or are inefficiently infected, some strains have been found which are efficiently infected. Temperature may also affect the infection capability of mycobacteriophage. For example, phAE42-12 will infect *M. fortuitum* and *M. gordonae* at temperatures greater than about 37° C.

Treatment with NAP can reduce the luminescence signal 5–10 fold or more in TB complex organisms with little or no effect on the high levels of luminescence signal from LRM-infected MOTT, regardless of whether the infection is due to lack of infection specificity or is induced by higher temperatures. This differential effect has now been used to determine whether or not a positive signal in a reporter mycobacteriophage assay for TB complex organisms is indicative of a TB complex organism or MOTT. The invention therefore increases the utility of reporter phage constructions, as perfect infection specificity for the TB complex is no longer required for a useful clinical diagnostic test. Sometimes a minor reduction in the luminescence signal is seen initially in LRM infected MOTT treated with NAP, however, this reduction is less than 5-fold and the organisms often recover. Therefore, a substantial reduction in signal (defined as a reduction in signal of about 5-fold or more) is indicative of TB complex mycobacteria.

A typical assay for distinguishing species of mycobacteria according to the invention is performed as follows. Log phase cultures of the mycobacteria to be identified are exposed to NAP under conditions appropriate for continued growth of the culture. For mycobacteria, growth conditions are typically a liquid medium conventionally used for growth of mycobacteria (e.g., Lowenstein Jensen media, 7H9 or BACTEC liquid media) and an incubation temperature of about 37° C. The culture is exposed to an amount of NAP sufficient to inhibit growth of TB complex organisms if they are present. A NAP concentration of 0.5–100 μg/ml is typically sufficient to inhibit growth of TB complex mycobacteria. The culture may be infected with the RM either simultaneously with exposure to NAP, or the culture may be incubated for a period of time in the presence of NAP prior to infection with the RM. Typically, cultures are incubated in the presence of NAP for about 1–48 hours to ensure that growth of TB complex mycobacteria, if present, is inhibited. However, as illustrated in Example 2, the period of exposure to NAP in many cases may be as short as 1–3 hours. It is only necessary that the exposure to NAP be long enough to result in a detectable reduction in luminescence or β-galactosidase reaction product in TB complex mycobacteria in the RM assay. If the culture medium contains a detergent, the cells must be pelleted, washed and resuspended in a medium which does not contain a detergent prior to mycobacteriophage infection. The RM are then added to the culture (with NAP if the cells were not previously exposed) and incubated at about 35°–50° C. for a period of time to allow phage infection. Typically, about 1–5 hours is allowed for infection, however, the time for infection can be routinely optimized and adjusted for a particular RM/NAP assay system. The luminescence of LRM-infected cells is then determined upon addition of luciferin, measuring light emission in a luminometer. If a β-GRM is used, the colorimetric or fluorometric substrate is added and incubated with the β-GRM infected cells for a period of time sufficient for the enzymatic reaction to occur (typically several hours or overnight). The amount of the reaction product is then determined qualitatively or quantitatively. Colored reaction products may be detected, for example, visually or by optical density. Fluorescence may be detected, for example, visually or by instrumentation.

The above assay for distinguishing species of mycobacteria may be included in protocols for antibiotic susceptibility testing (AST) of mycobacteria to determine whether or not an antibiotic-resistant strain is an antibiotic-resistant TB complex mycobacterium or antibiotic-resistant MOTT. This allows identification of the mycobacterium at essentially the same time as its antibiotic susceptibility is determined. For example, a clinical specimen suspected of containing a species of mycobacteria may be cultured and then tested in parallel in the NAP RM assay of the invention and in an RM assay for antibiotic susceptibility, for example the LRM assay described by Jacobs, et al., supra. After culturing, several subcultures are prepared: 1) a subculture containing 0.5–100 μ/ml NAP, 2) at least one subculture containing an antibiotic (e.g., streptomycin, isoniazid, rifampicin or ethambutol), and 3) a control subculture containing neither antibiotic or NAP. After incubation of the subcultures for a period of time to allow NAP and the antibiotics to take effect, the control, NAP and antibiotic subcultures are infected with an RM as described above. Typically, the subcultures are infected about 48 hours after subculturing so that the NAP result and the antibiotic sensitivity result are available at approximately the same time. The luminescence of LRM-infected cells or reaction product produced by β-GRM infected cells is then determined as described above, and the signal in the NAP and antibiotic subcultures is compared to the uninhibited control. If signal is substantially reduced or absent in the NAP subculture, the mycobacterium present in the clinical sample is a member of the TB complex. If the RM signal is also reduced or absent in one or more of the antibiotic subcultures, that TB complex mycobacterium is also sensitive to the antibiotic present in the subculture or subcultures in which the signal is reduced or absent. If the RM signal is comparable to the control in the NAP subculture and reduced or absent in one or more of the antibiotic subcultures, the mycobacterium is a MOTT which is sensitive to the antibiotic present in the subculture or subcultures in which the signal is reduced or absent. Antibiotic-resistant TB complex mycobacteria produce levels of signal comparable to the control in the subculture(s) containing the antibiotic(s) to which they are resistant, but signal would be reduced or absent in the NAP subculture. Antibiotic-resistant MOTT produce levels of RM signal comparable to the control in the subculture(s) containing the antibiotic(s) to which they are resistant and in the NAP subculture. Of course, a microorganism may be resistant to one concentration of an antibiotic but sensitive at higher concentrations. The level of resistance or sensitivity may be determined by adjusting the concentration of antibiotic in the subcultures in the methods of the invention.

The effect of NAP on TB complex mycobacteria can be detected in the RM assay with 1–3 hours exposure to NAP, whereas longer exposure to the antibiotic (e.g., 48 hours) may be required to detect sensitivity or resistance. For this reason, it may be useful to first determine whether or not a clinical specimen contains TB complex mycobacteria using the NAP RM assay and subsequently determine antibiotic sensitivity if TB complex mycobacteria are found to be present. In this way, a clinician will know within a few hours whether or not clinically relevant TB complex mycobacteria are present in a specimen.

The invention improves RM assays by simplifying the interpretation of assay results for identification of mycobacterial species and significantly shortening the time required to obtain these results. The conventional BACTEC NAP identification system is not begun until the culture reaches GI 50, and then requires an additional 4–6 days to complete. Results may be obtained using the inventive methods in approximately the same amount of time as in probe-based hybridization systems for identification of mycobacteria (often 3 hours or less). In addition, antibiotic susceptibility testing (AST) using the RM/NAP methods of the invention provides a time savings of about 5–8 days (starting from BACTEC cultures) as compared to conventional BACTEC AST protocols. The conventional BACTEC AST is begun when the culture reaches GI 500 and then requires an additional 5–6 days to complete. Conventional AST on solid media requires even longer time periods than conventional BACTEC AST to obtain a result. In contrast, AST performed with the RM assay of the invention begins at GI <500 (typically GI less than about 250) and can be completed in 1–2 additional days.

EXAMPLE 1

Representative TB complex organisms (*M. bovis bcg* and *M. tuberculosis* strain 201) and various mycobacteria other than tuberculosis were differentiated using LRM detection with and without NAP treatment. The growth of the test mycobacteria on Lowenstein Jensen slants was standardized by inoculation into BACTEC liquid media, subculturing when necessary to obtain log phase cultures at moderate growth index (typically GI 100–300). BACTEC culture bottles containing 5 μg/ml NAP were prepared by addition of 0.1 ml of 200 μg/ml NAP to each 4.0 ml bottle. The organism to be tested was subcultured into BACTEC culture bottles with or without NAP by addition of 0.5 ml of the liquid culture to each bottle. Subculture bottles containing NAP were incubated at 37° C. for an additional 24–48 hours, monitoring GI daily. The luciferase phage assay was then performed using phage phAE42-12, comparing the luminescence signals obtained from infections of NAP treated organisms with untreated organisms, as follows.

After the NAP treatment period, media were removed and the organisms in each culture bottle were washed. Cells were pelleted by centrifugation at 1500 xg for 15 minutes at room temperature and resuspended in room temperature 7H9 medium (Difco) containing 0.2% glycerol and 10% ADC (5% albumin/2% dextrose/145 mM sodium chloride). The cells were washed a second time as before, resuspending the cells in a final volume of 350 μgl 7H9. To initiate infection, phage phAE42-12 were added in a volume of 7.5 μl to give $4\times10^9$ pfu/ml and incubated at 37° C. for 3 hours. The luminescence signal was measured after 3 hours of infection by transferring 100 μl of phage-infected cells to a luminometer cuvette and adding 100 μl of 1 mM luciferin in 0.1 M sodium citrate pH 4.5. Light emission was measured immediately after addition of these reagents, integrating the signal for 15 seconds. Luminescence was measured as the ratio of luminescence signal to background luminescence in uninfected cultures. A ratio of signal to background of 2 or greater is considered positive for light production by the LRM.

To assess the effect of temperature on the assay, similar experiments were performed with phage infection at 47° C. For several MOTT the signal was higher for infections at 47° C. as compared to infections at 37° C. NAP treatment had little effect on the luminescence signal generated by these organisms, regardless of the temperature of phage infection. However, the signal from untreated TB complex organisms was greatly reduced with infection at 47° C. as compared to untreated TB complex organisms infected at 37° C.

The luminescence signal from TB complex organisms was substantially reduced by more than 1 log by pretreating with 5 μg/ml NAP for 24–48 hours. For MOTT the signal was essentially unchanged by NAP pretreatment. The results are shown in the following Table:

| Mycobacterium | NAP 5 μg/ml | NAP Exposure (hrs.) | Luminescence (Signal/Background |
|---|---|---|---|
| | TB COMPLEX | | |
| TB201 | − | 24 | 27 |
| | + | | 3.9 |
| | − | 48 | 32 |
| | + | | 1 |
| BCG | − | 48 | 5650 |
| | + | | 4 |
| BCG | − | 48 | 120 |
| | + | | 0.9 |
| BCG | − | 48 | 100 |
| | + | | 1.1 |
| BCG | − | 48 | 138 |
| | + | | 1.2 |
| BCG | − | 48 | 169 |
| | + | | 1.3 |
| BCG | − | 48 | 378 |
| | + | | 2.4 |
| | MOTT | | |
| xenopi | − | 24 | 1 |
| | + | | 1 |
| | − | 48 | 1.9 |
| | + | | 1.1 |
| kansasii | − | 24 | 1.3 |
| | + | | 1.7 |
| | − | 48 | 2.4 |
| | + | | 2.1 |
| avium 1546 | − | 24 | 1.3 |
| | + | | 1.4 |
| | − | 48 | 5.6 |
| | + | | 4.2 |
| flavescens | − | 24 | 13 |
| | + | | 12 |
| | − | 48 | 51 |
| | + | | 33 |
| smegmatis >37° C. | − | 24 | 580 |
| | + | | 1132 |
| | − | 48 | 135 |
| | + | | 403 |
| fortuitum >37° C. | − | 24 | 57 |
| | + | | 96 |

-continued

| Mycobacterium | NAP 5 μg/ml | NAP Exposure (hrs.) | Luminescence (Signal/Background |
|---|---|---|---|
| | – | 48 | 221 |
| | + | | 184 |
| gordonae >37° C. | – | 24 | 42 |
| | + | | 50 |
| | – | 48 | 146 |
| | + | | 164 |
| chelonae >37° C. | – | 24 | 1.2 |
| | + | | 1.1 |
| | – | 48 | 1.24 |
| | + | | 1.25 |
| gastri #2978 | – | 48 | 9.9 |
| | + | | 10 |
| gastri #2977 | – | 48 | 2.1 |
| | + | | 2.0 |
| gastri #2973 | – | 48 | 5.3 |
| | + | | 3.3 |
| fortuitum 37° C. | – | 48 | 1.1 |
| | + | | 1.1 |
| gordonae 37° C. | – | 48 | 1.0 |
| | + | | 0.9 |
| smegmatis 37° C. | – | 48 | 67 |
| | + | | 34 |
| chelonae 37° C. | – | 48 | 1.9 |
| | + | | 2.6 |
| intracellulare | – | 48 | 37 |
| (Edgar B.) | + | | 27 |
| intracellulare | – | 48 | 13 |
| (P-54) | + | | 16 |

As expected, *M. fortuitum, M. gordonae, M. avium, M. kansasii* and *M. xenopi* showed little or no infection by the LRM. Any low levels of luminescence detected in these species were essentially unchanged by treatment with NAP. MOTT strains which showed significant levels of infection by LRM were *M. flavescens, M. smegmatis, M. chelonae, M. intracellulare*, and *M. fortuitum* and *M. gordonae* at higher temperatures. The luminescence produced by these organisms was also essentially unaffected by treatment with NAP. In contrast, the luminescence signals of *M. tuberculosis* and *M. tuberculosis BCG* were high in the absence of NAP treatment but were substantially reduced to near or below 2 (an essentially negative signal/background) by treatment with NAP.

EXAMPLE 2

*M. bovis BCG* and phage phAE42-12 were used to measure the kinetics of the NAP effect on detection of TB complex organisms using LRM, comparing treatment with 5 μg/ml and 10 μg/ml NAP. Seven day roller bottle cultures of BCG were grown in 7H9 media containing 0.2% glycerol, 10% ADC and 0.01% TWEEN-80. The cells were washed twice in the same medium but without TWEEN-80 as described in Example 1. The cells were then diluted to a density of $10^7$ cells/ml for phage infection. In some samples NAP was added at the same time as the phage for 3 hours. In other samples NAP was added before or after phage to obtain treatment times varying from 0–5 hours. All luminescence assays were performed as in Example 1 at 3 hours post infection. The results are shown in FIG. 1.

Three hours of NAP treatment, obtained by simultaneous addition of NAP and phage phAE42-12, was sufficient to reduce the luminescence signal more than 10 fold. However, the time course of reduction in luminescence shown in FIG. 1 indicates that the reduction in signal would be substantial and easily detectable in as little as 1 hour (about a 5-fold reduction). This rapid effect of NAP indicates that the method of the invention provides an identification test which can identify TB complex organisms in three hours or less with a simple workflow. This is in contrast to prior art methods in which the effect of NAP on culture growth is followed by monitoring $CO_2$ production, requiring 4–6 days for species identification.

EXAMPLE 3

Figure 2:
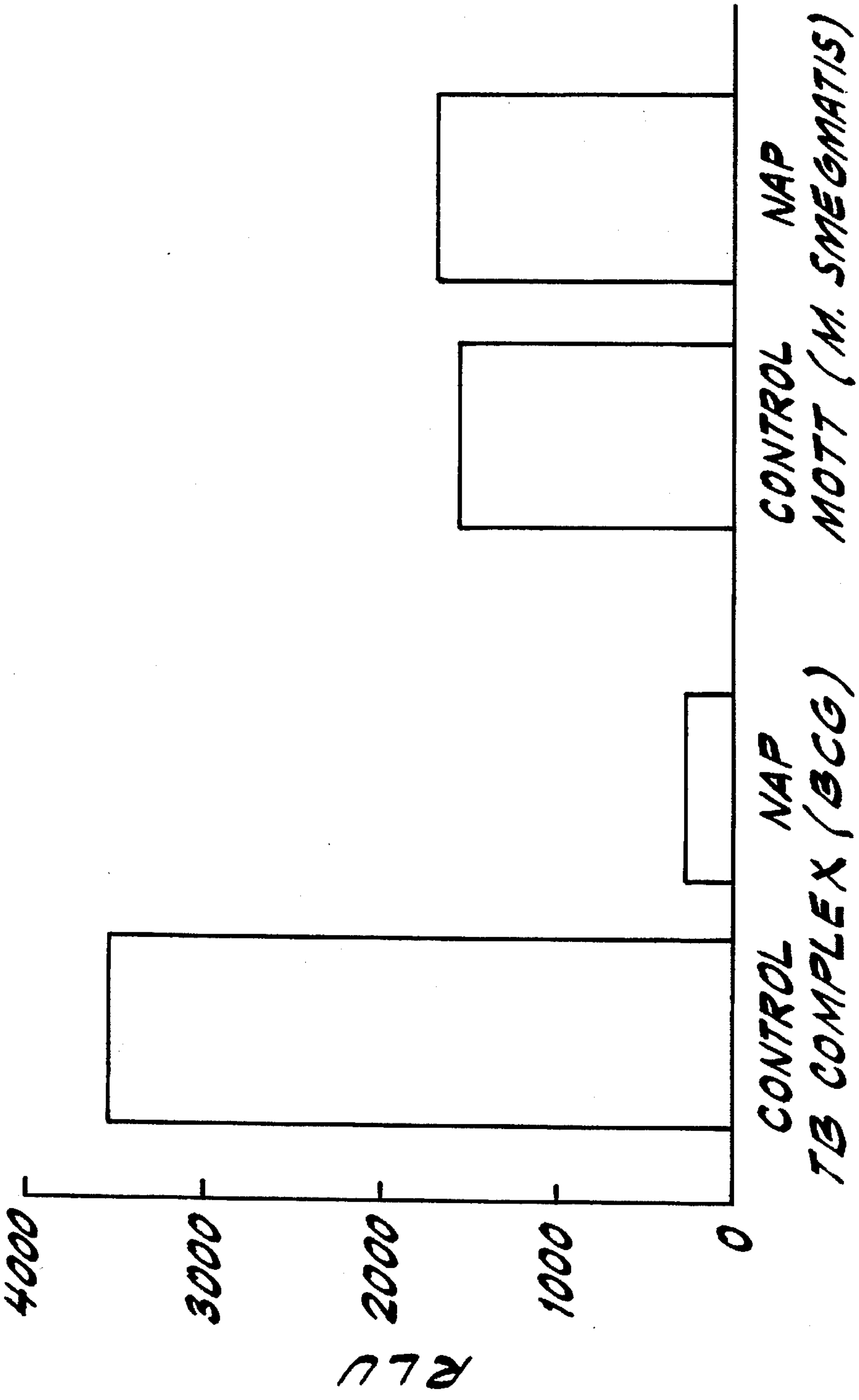
FIG. 2 compares the effect of NAP on luminescence generated by an LRM-infected TB complex species to luminescence generated by an LRM-infected MOTT species.

The methods of the invention were used to distinguish between a TB complex species (*M. bovis BCG*) and a MOTT species (*M. smegmatis*) in about three hours. Seven day roller bottle cultures of these species were grown in 7H9 media containing 0.2% glycerol, 10% ADC and 0.01% TWEEN-80. The cells were washed twice in the same medium but without TWEEN-80 as described in Example 1. The cells were then diluted to a density of $10^7$/ml for phage infection. NAP (5 μg/ml) was added at the same time as phage. Luminescence assays were performed as in Example 1 at 3 hours post infection. The results are shown in FIG. 2. Luminescence in *M. smegmatis* was essentially unchanged in the presence of NAP, however, luminescence in *M. bovis BCG* was reduced about 14-fold, providing a clear distinction between the TB complex species and the MOTT species.

EXAMPLE 4

The FFluc gene of phAE40 (expressed from a heat shock protein "hsp" promoter) was removed and replaced with the β-galactosidase gene (LacZ) for use as a β-GRM in the NAP assay. This phage was identified as phAE40-LACZ. Colorimetric systems such as this are useful for situations in which instrumentation, such as a luminometer, is not readily available. Seven day roller bottle cultures of *M. bovis BCG* and overnight log phase cultures of *M. smegmatis* in 7H9 with 10% ADC and 0.01% TWEEN-80 were centrifuged to pellet the cells and washed twice with 7H9 medium. Assays were set up for each species at $10^8$ cells/ml, $10^7$ cells/ml and $10^6$ cells/mi. These samples were infected with phAE40-LACZ at $2\times10^{10}$ pfu/ml, simultaneously adding 5 μg/ml or 10 μg/ml NAP. Infection was allowed to proceed for 2 hours at 37° C. Uninfected controls and infected controls without NAP treatment were also included in the analysis.

Following infection, X-Gal was added to a final concentration of 0.02% and the samples were incubated overnight to allow color development. The intensity of the blue color produced was evaluated visually and by reading absorbance at 620 nm ($A_{620}$). Inhibition of color development in the BCG samples was generally not as complete as inhibition of luminescence in the LRM assay. However, it was possible to differentiate BCG from MOTT visually, particularly at lower cell concentrations ($10^6$ cells/ml), where an estimated 4–5-fold reduction in signal was observed after treatment with either 5 μg/ml or 10 μml NAP. As cell concentration increased, the difference in color production between the two species became less distinct. The variable effect of NAP on culture growth depending on cell density ("inoculum effect") has been previously observed in other NAP assay systems, and is not believed to be due to any feature of this particular assay. Absorbance readings were also more variable than those obtained in the LRM assay, but the signal/background ratios were generally lower for BCG treated with NAP than for *M. smegmatis* treated with NAP.

The above experiment was repeated, substituting chlorophenol red-β-D-galactopyranoside for X-gal as the colorimetric enzyme substrate. Similar results were obtained, however, reduction in the reaction product could be detected in several hours. This substrate may therefore provide a more sensitive detection system than X-gal. It is expected that the β-GRM assay system cab be improved by further optimization of parameters such as the time of substrate addition, and the time and dose for NAP treatment. It is also expected that other colorimetric or fluorometric substrates for β-galactosidase may be routinely used in this assay to distinguish TB complex organisms from MOTT.

β-galactosidase is much more stable in the cell than luciferase, and it was therefore unexpected that a reduction in the amount of reaction product could be detected in this system within several hours of exposure to NAP. Further, the β-galactosidase signal generating system does not require ATP for signal production as luciferase does. It was therefore uncertain whether NAP treatment would result in a reduction in β-galactosidase reaction product at all. The discovery that two reporter genes with such different enzymatic mechanisms can be used in the RM assay of the invention suggests that the effect of NAP on growth of TB complex mycobacteria may affect multiple biochemical processes specific to TB complex organisms.

What is claimed is:

1. A method for distinguishing species of mycobacteria in a sample comprising:

a) treating the mycobacteria with α-p-nitro-β-acetylamino-β-hydroxy-propiophenone (NAP) in an amount sufficient to inhibit growth of a tuberculosis (TB) complex species;

b) infecting the mycobacteria with a luciferase reporter mycobacteriophage which infects the TB complex species and at least one mycobacteria other than tuberculosis (MOTT) species, the luciferase reporter mycobacteriophage producing a luminescence signal in the presence of luciferin upon growth of mycobacteria infected with the luciferase reporter mycobacteriophage;

c) contacting the infected mycobacteria with luciferin, whereby the luminescence signal produced by the luciferase reporter mycobacteriophage is substantially reduced when the NAP-treated TB complex species is infected with the luciferase reporter mycobacteriophage, and;

d) distinguishing the TB complex species from the MOTT species by the reduced luminescence signal.

2. The method of claim 1 wherein the mycobacteria are treated with 0.5–100 μg/ml NAP.

3. The method of claim 2 wherein the mycobacteria are treated with 5 μg/ml NAP.

4. The method of claim 2 wherein the mycobacteria are treated with NAP for 1–48 hours.

5. The method of claim 2 wherein the mycobacteria are infected for 1–5 hours.

6. The method of claim 5 wherein the mycobacteria are infected for about 3 hours.

7. The method of claim 1 further comprising testing the mycobacteria in the sample for antibiotic susceptibility in an luciferase reported mycobacteriophage (LRM) assay.

8. A method for distinguishing species of mycobacteria in a sample comprising:

a) infecting the mycobacteria with a luciferase reporter mycobacteriophage in the presence of an amount of α-p-nitro-β-acetylamino-β-hydroxy-propiophenone (NAP) sufficient to inhibit growth of a tuberculosis (TB) complex species, the luciferase reporter mycobacteriophage infecting the TB complex species and at least one mycobacteria other than tuberculosis (MOTT) species and producing a luminescence signal in the presence of luciferin upon growth of mycobacteria infected with the luciferase reporter mycobacteriophage;

b) contacting the infected mycobacteria with luciferin, whereby the luminescence signal produced by the luciferase reporter mycobacteriophage is substantially reduced when the NAP-treated TB complex species is infected with the luciferase reporter mycobacteriophage, and;

c) distinguishing the TB complex species from the MOTT species by the reduced luminescence signal.

9. The method of claim 8 wherein the mycobacteria are infected in the presence of 0.5–100 μg/ml NAP.

10. The method of claim 9 wherein the mycobacteria are infected in the presence of 5 μg/ml NAP.

11. The method of claim 9 wherein the mycobacteria are infected in the presence of NAP for 1–5 hours.

12. The method of claim 11 wherein the mycobacteria are infected for about 3 hours.

13. The method of claim 8 further comprising testing the mycobacteria in the sample for antibiotic susceptibility in an luciferase reporter mycobacteriophage (LRM) assay.

14. A method for distinguishing species of mycobacteria in a sample comprising:

a) treating the mycobacteria with α-p-nitro-β-acetylamino-β-hydroxy-propiophenone (NAP) in an amount sufficient to inhibit growth of a tuberculosis (TB) complex species;

b) infecting the mycobacteria with a β-galactosidase reporter mycobacteriophage which infects the TB complex species and at least one mycobacteria other than tuberculosis (MOTT) species, the β-galactosidase reporter mycobacteriophage producing a signal in the presence of a colorimetric or fluorometric substrate for β-galactosidase upon growth of mycobacteria infected with the β-galactosidase reporter mycobacteriophage;

c) contacting the infected mycobacteria with the colorimetric or fluorometric substrate, whereby the signal produced by the β-galactosidase reporter mycobacteriphage is substantially reduced when the NAP-treated TB complex species is infected with the β-galactosidase reporter mycobacteriophage, and;

d) distinguishing the TB complex species from the MOTT species by the reduced signal.

15. The method of claim 14 wherein the mycobacteria are treated with 0.5–100 μg/ml NAP.

16. The method of claim 15 wherein the mycobacteria are treated with 5 μg/ml NAP.

17. The method of claim 15 wherein the mycobacteria are treated with NAP for 1–48 hours.

18. The method of claim 15 wherein the mycobacteria are infected for 1–5 hours.

19. The method of claim 18 wherein the mycobacteria are infected for about 3 hours.

20. The method of claim 14 wherein the colorimetric or fluorometric substrate is selected from the group consisting of 5-bromo-4-chloro-3-indolyl-β-D-galactoside (X-gal), chlorophenol red-β-D-galactopyranoside and methyl umbelliferyl-β-D-galactopyranoside.

21. The method of claim 14 further comprising testing the mycobacteria in the sample for antibiotic susceptibility in a β-galactosidase reporter mycobacteriophage assay.

22. A method for distinguishing species of mycobacteria in a sample comprising:

a) infecting the mycobacteria with a β-galactosidase reporter mycobacteriophage in the presence of an amount of α-p-nitro-β-acetylamino-βhydroxy-propiophenone (NAP) sufficient to inhibit growth of a tuberculosis (TB) complex species, the β-galactosidase reporter mycobacteriophage infecting the TB complex species and at least one mycobacteria other than tuberculosis (MOTT) species and producing a signal in the presence of a colorimetric or fluorometric substrate for β-galactosidase upon growth of mycobacteria infected with the β-galactosidase reporter mycobacteriophage;

b) contacting the infected mycobacteria with the colorimetric or fluorometric substrate, whereby the signal produced by the β-galactosidase reporter mycobacteriophage is substantially reduced when the NAP-treated TB complex species is infected with the β-galactosidase reporter mycobacteriophage, and;

c) distinguishing the TB complex species from the MOTT species by the reduced signal.

23. The method of claim 22 wherein the mycobacteria are infected in the presence of 0.5–100 μg/ml NAP.

24. The method of claim 23 wherein the mycobacteria are infected in the presence of 5 μg/ml NAP.

25. The method of claim 23 wherein the mycobacteria are infected for 1–5 hours.

26. The method of claim 25 wherein the mycobacteria are infected for about 3 hours.

27. The method of claim 22 wherein the colorimetric or fluorometric substrate is selected from the group consisting of 5-bromo-4-chloro-3-indolyl-β-D-galactoside (X-gal) chlorophenol red-β-D-galactopyranoside and methyl umbelliferyl-β-D-galactopyranoside.

28. The method of claim 22 further comprising testing the mycobacteria in the sample for antibiotic susceptibility in a β-galactosidase reporter mycobacteriophage assay.

29. A method for distinguishing species of mycobacteria in a sample comprising:

a) treating the mycobacteria with α-p-nitro-β-acetylamino-β-hydroxy-propiophenone (NAP) in an amount sufficient to inhibit growth of a tuberculosis (TB) complex species;

b) infecting the mycobacteria with a reporter mycobacteriophage which infects the TB complex species and at least one mycobacteria other than tuberculosis (MOTT) species, the reporter mycobacteriophage producing a signal upon growth of mycobacteria infected with the reporter mycobacteriophage;

c) causing the reporter mycobacteriophage to produce a signal, whereby the signal produced by the reporter, mycobacteriophage is substantially reduced when the NAP-treated TB complex species is infected with the reporter mycobacteriophage, and;

d) distinguishing the TB complex species from the MOTT species by the reduction in the signal.

30. A method for distinguishing species of mycobacteria in a sample comprising:

a) infecting the mycobacteria with a reporter mycobacteriophage in the presence of an amount of α-p-nitro-β-acetylamino-β-hydroxy-propiophenone (NAP) sufficient to inhibit growth of a tuberculosis (TB) complex species, the reporter mycobacteriophage infecting the TB complex species and at least one mycobacteria other than tuberculosis (MOTT) species and producing a signal upon growth of mycobacteria infected with the reporter mycobacteriophage;

b) causing the reporter mycobacteriophage to produce a signal, whereby the signal produced by the reporter mycobacteriophage is substantially reduced when the NAP-treated TB complex species is infected with the reporter mycobacteriophage, and;

c) distinguishing the TB complex species from the MOTT species by the reduced signal.

* * * * *